United States Patent [19]
Johnson

[11] Patent Number: 5,334,352
[45] Date of Patent: Aug. 2, 1994

[54] MANIFOLD CONSTRUCTION

[75] Inventor: Edgar G. Johnson, Huntsville, Ala.

[73] Assignee: ICN Biomedicals, Inc., Costa Mesa, Calif.

[21] Appl. No.: 950,430

[22] Filed: Sep. 23, 1992

[51] Int. Cl.$^5$ .............. B01L 3/00; B05B 1/14
[52] U.S. Cl. ................... 422/99; 422/100; 137/561 A; 239/553; 239/566
[58] Field of Search ......... 137/561 A; 422/99, 100, 422/103; 239/193, 552, 553, 553.5, 566

[56] References Cited

U.S. PATENT DOCUMENTS

| | | | |
|---|---|---|---|
| 3,572,552 | 3/1971 | Guinn | 422/100 X |
| 3,795,259 | 3/1974 | Brandin et al. | 137/561 A |
| 4,185,780 | 1/1980 | Duchene et al. | 239/553.5 |
| 4,198,482 | 4/1980 | Homer | 422/100 X |
| 4,302,338 | 11/1981 | Pfohl et al. | 137/561 A X |
| 4,528,919 | 7/1985 | Harbolt et al. | 137/561 A X |
| 4,549,567 | 10/1985 | Horton | 137/561 A X |
| 4,759,382 | 7/1988 | Harel | 137/561 A X |
| 4,779,467 | 10/1988 | Rainin et al. | 422/100 X |
| 4,781,309 | 11/1988 | Vogel | 137/561 A X |
| 5,095,930 | 3/1992 | Stroszynski et al. | 137/561 A X |
| 5,099,879 | 3/1992 | Baird | 137/561 A |
| 5,101,847 | 4/1992 | Oribe | 137/561 A X |
| 5,103,863 | 4/1992 | Powers | 137/561 A |
| 5,117,864 | 6/1992 | Byers | 137/561 A |
| 5,264,036 | 11/1993 | Haas et al. | 239/553.5 X |

Primary Examiner—James C. Housel
Assistant Examiner—Milton I. Cano
Attorney, Agent, or Firm—Lyon & Lyon

[57] ABSTRACT

A manifold with improved flow-splitting characteristics, resulting in uniform or nearly uniform flows from its outlet passages, is provided. The internal flow dynamics of the manifold are adjusted by modifying the cross-sectional area of the elongated manifold cavity. The cross-sectional area may be modified by placing one or more inserts in the interior cavity of the manifold, each insert having a nonconstant cross-sectional area designed to compensate for the differential flow characteristics within the manifold. Alternatively, the interior of the manifold may be formed with a nonconstant cross-sectional area designed to compensate for the differential flow characteristics within the manifold.

6 Claims, 2 Drawing Sheets

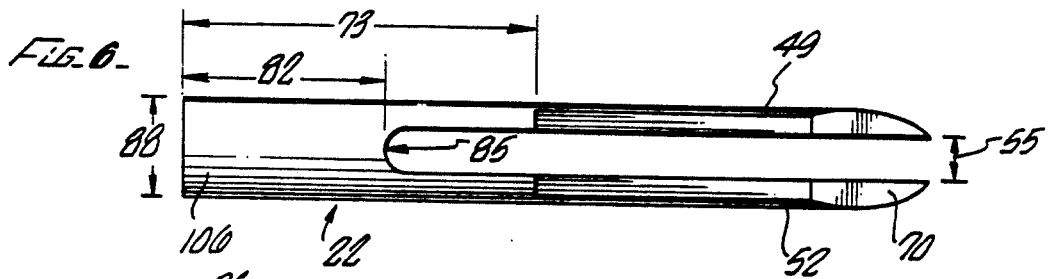
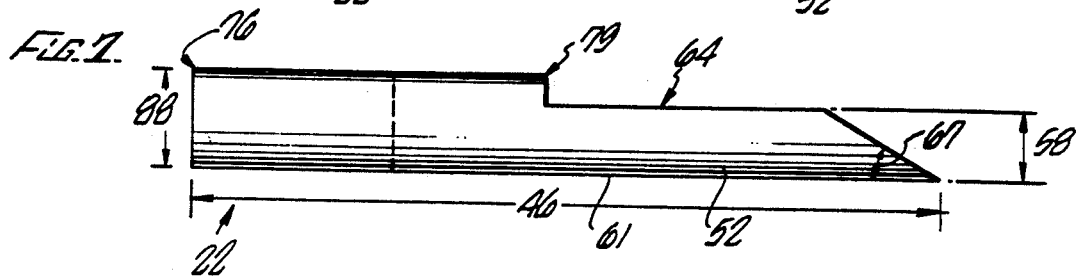
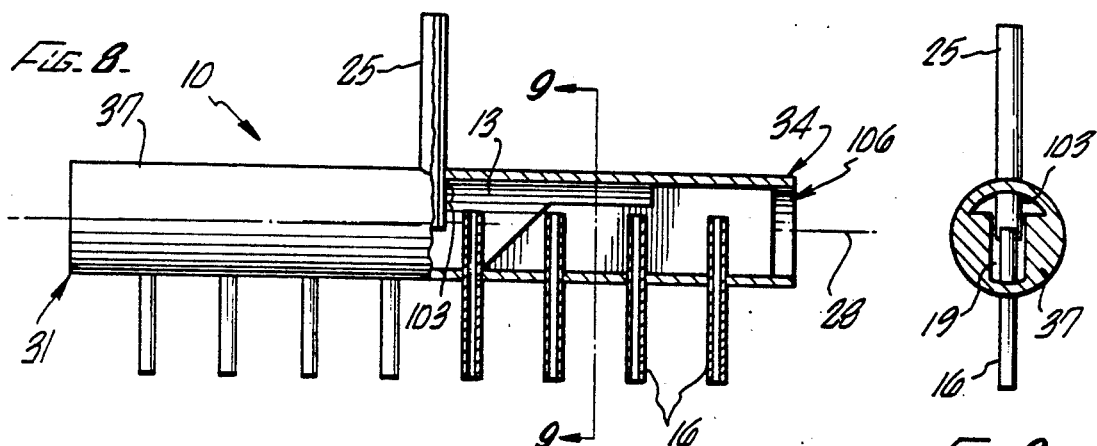
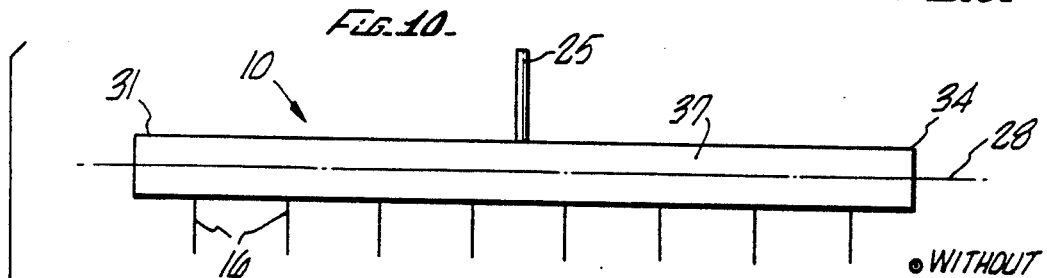
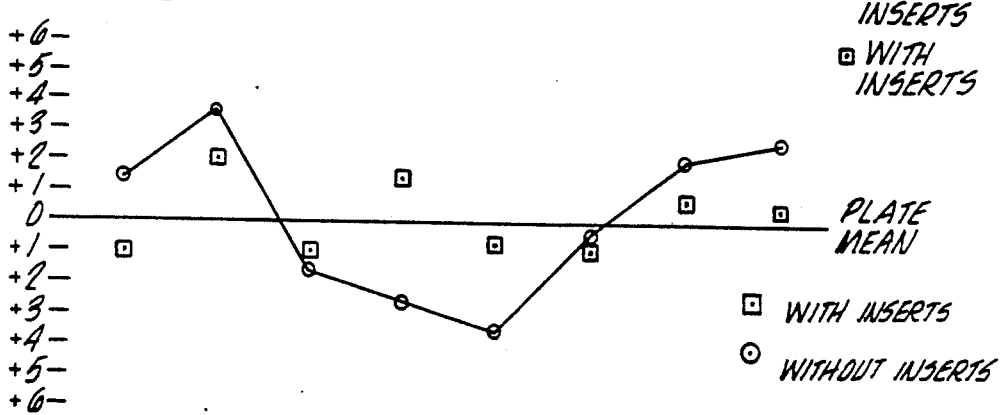

MANIFOLD CONSTRUCTION

BACKGROUND OF THE INVENTION a. Field of the Invention

The field of the invention pertains to manifolds for splitting a fluid flow, more specifically, manifolds that uniformly split fluid from an inlet passage among a multiplicity of outlet passages.

b. Background Art

Splitting a quantity of fluid into equal portions is useful for many reasons. For example, a sample of fluid may be evenly distributed among the wells of a microtitration plate ("plate" or "microplate") or among a group of test tubes. In this manner, research may be conducted on several uniform samples at the same time, accelerating the research and allowing for direct correlation of results.

One existing method used to split a quantity of fluid into approximately equal portions involves dedicating a costly pump or syringe to each outlet passage. A common and less expensive method used for dispensing fluid into a microplate entails passing the fluid through a manifold. The instant invention relates to this latter method.

Customarily, a manifold comprises multiple ports or passages inserted into an elongated cylindrical cavity. Fluid is introduced into the cavity and subsequently dispersed through outlet ports into a receptacle (e.g., a microplate). A manifold with only two symmetrically placed outlet passages would have a nearly equal flow from its outlet passages. However, manifolds with more than two outlet passages are the most useful, and the more outlet passages, the greater the flow disparity.

In a typical manifold, the number of outlet passages is designed to match the number of wells in a single column of a microplate, which has several columns of wells. In this manner, the manifold may fill the microplate one column at a time. Thus, Manifolds having either eight or twelve outlet passages are common. The outlet passages are positioned, not necessarily symmetrically, on each side of the inlet passage. Accordingly, the flow from each of the outlet passages is not uniform in the absence of a flow modifying device such as the instant invention.

In the operation of a typical manifold for microplate dispersion applications, the manifold is first primed to eliminate the manifold's "dead volume" (i.e., the volume of fluid needed to fill the manifold before useful dispensing can start). Then, a volume of fluid equal to the volume desired for each well in a single column of the microplate times the number of outlet passages (which equals the number of wells in a single column of wells), is dispensed into the inlet passage of the manifold. Ideally, the manifold then evenly disperses the flow among the microplate wells of the column. However, the flow from the outlet passages nearest the inlet passage is typically less than the flow from the outlet passages most distant from the inlet passage. This discrepant flow pattern results from the internal flow dynamics of the manifold, which must be adjusted to balance the flow.

SUMMARY OF THE INVENTION

The instant invention adjusts the internal flow dynamics of a manifold by modifying the cross-sectional area of the elongated manifold cavity. Modification of the cross-sectional area may be achieved in a number of ways. One or more inserts may be placed in the interior cavity of the manifold, each insert having a nonconstant cross-sectional area designed to compensate for the differential flow characteristics within the manifold. Alternatively, the interior of the manifold itself may be formed with a nonconstant cross-sectional area designed to compensate for the differential flow characteristics within the manifold.

In a first preferred embodiment, the manifold has multiple outlet passages and a single inlet passage perpendicular or parallel to the longitudinal axis of the manifold main body. The flow dynamics are modified in this embodiment either by inserting one insert into each end of the manifold cavity or by inserting a single longer insert into one end of the cavity. This arrangement makes it possible to use the common and inexpensive method of pressing multiple ports or passages into an elongated cylindrical cavity to make a manifold and yet allows the user to compensate for the otherwise disparate flow from the outlet passages.

In another preferred embodiment, the inserts are, in effect, built into the interior walls of the manifold cavity. In this embodiment, the flow dynamics are adjusted by the shape of the interior of the cavity itself, and no inserts are required.

Accordingly, it is an object of the disclosed invention to provide a relatively inexpensive manifold with improved flow-splitting characteristics, resulting in uniform or nearly uniform flows among its outlet passages. The instant invention can achieve this objective while reducing the "dead volume" of the manifold. Other objects of the disclosed invention will be apparent from the following description.

BRIEF DESCRIPTION OF THE DRAWINGS

The present invention will be understood more fully from the detailed description given below and from the accompanying drawings of the preferred embodiments of the invention. The drawings should not be taken to limit the invention to these specific embodiments, but are for explanation and understanding only.

FIGS. 6 and 7 illustrate two views, one rotated 90 degrees about the longitudinal axis of the other one, of an insert that may be used with a manifold in accordance with a first embodiment of the present invention;

FIG. 8 is a view in partial section of a manifold in accordance with a second embodiment of the present invention;

FIG. 9 is a second view of the manifold depicted in FIG. 8, taken along section 9—9 of that figure; and FIG. 10 is a plot portraying the beneficial effect of altering the flow within the manifold according to a first embodiment of the present invention.

DESCRIPTION OF THE PREFERRED EMBODIMENTS

Figure 1:
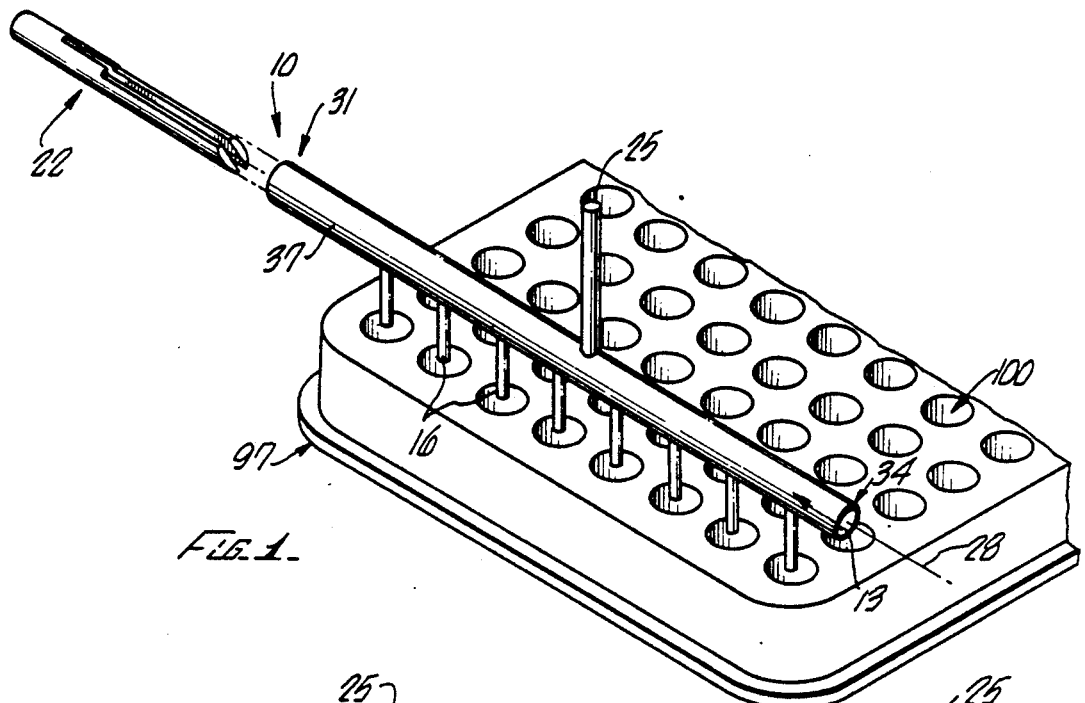
FIG. 1 is a perspective view of a first embodiment of the present invention with an insert removed from one end, shown above a partial drawing of an eight row microtitration plate ("microplate" or "plate"), which could receive the fluid after it is uniformly divided by the manifold.

The flow dynamics within a manifold 10 may be changed by modifying the cross-sectional area of the manifold's elongated cavity 13. The following detailed description, taken in conjunction with the accompanying drawings, provides a further understanding of how the present invention modifies the cross-sectional area within a manifold 10 to balance the output from the outlet passages 16.

In a first preferred embodiment, shown in FIGS. 1–5, the cross-sectional area 19 of the elongated cavity 13 is adjusted by placing one or more inserts 22 into the cavity 13. In a second preferred embodiment, shown in FIGS. 8 and 9, an alternative method of adjusting the cross-sectional area 19 of the elongated cavity 13 is depicted. This latter method involves molding the elongated cavity 13 into a shape that compensates for the flow characteristics within the cavity 13.

Figure 2:
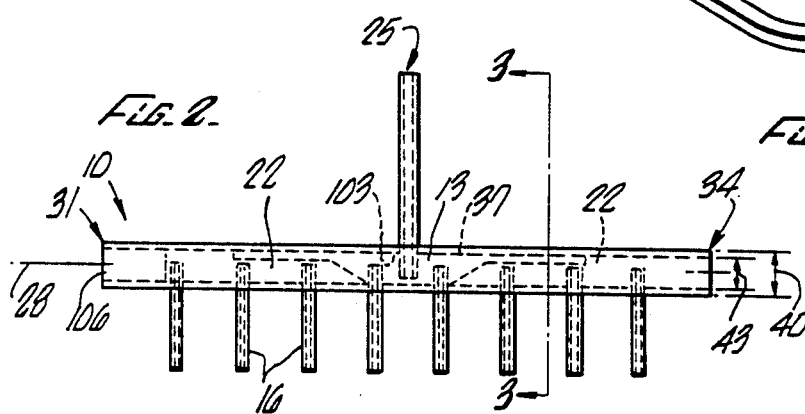
FIG. 2 is a view of a manifold in accordance with a first embodiment of the present invention from a direction perpendicular to the longitudinal axis of the manifold, showing internal features in phantom.
Figure 3:
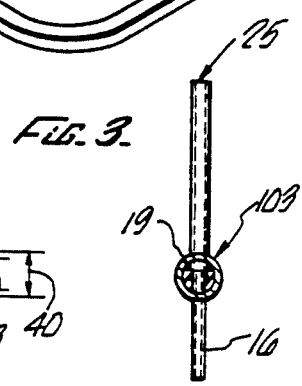
FIG. 3 is a second view of the manifold features depicted in FIG. 2, taken along section 3—3 of that figure.
Figure 4:
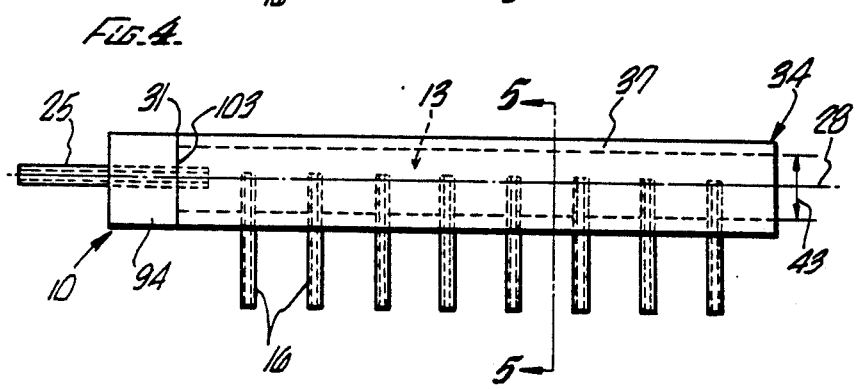
FIG. 4 illustrates a second manifold in accordance with a first embodiment of the present invention from a direction perpendicular to the longitudinal axis of the manifold, showing some internal features in phantom, but not showing an insert.
Figure 5:
FIG. 5 is a second view of the manifold features depicted in FIG. 4, taken along section 5—5 of that figure.

Referring initially to FIGS. 1–7, two variations of the first preferred embodiment of the present invention are described. The first variation is depicted in FIGS. 1–3, the second variation is depicted in FIGS. 4 and 5; and, although many shapes for insert 22 are possible, a typical insert 22 is depicted in FIGS. 6 and 7.

The first variation (with an inlet passage 25 perpendicular to the longitudinal axis 28) may employ one or two of the inserts 22 depicted in FIGS. 6 and 7. If a single insert 22 is used, it may be inserted into either the first end 31 or the second end 34 of the elongated cavity 13, and the insert 22 would span the distance between the ends 31, 34 of the cavity 13. Alternatively, as shown in FIG. 2, one insert 22 may be placed into the first end 31, and another insert 22 may be placed in the second end 34 of the manifold 10. In this latter configuration, one insert 22 spans the distance from the first end 31 approximately to the inlet passage 25, and the other insert 22 spans the distance from the second end 34 approximately to the inlet passage 25.

Assuming that two inserts are used and referring to FIGS. 1–3, 6, and 7, the construction of a manifold 10 according to a first variation of a first embodiment is now described. A main body 37, which spans approximately 3.3 inches from its first end 31 to its second end 34, is fashioned from a hollow tube (approximately 0.25 inches in main body outside diameter 40 and 0.178 inches in main body inside diameter 43), forming an elongated cavity 13 therein. Eight smaller tubes (approximately 0.045 inches in outside diameter) are then pressed into the bottom of the main body 37. The smaller tubes form the outlet passages 16 of the manifold 10 and split the flow from the inlet passage 25. These outlet passages 16 are approximately 0.6 inches in total length and protrude approximately 0.45 inches away from the exterior surface of the main body 37. Another tube (approximately 0.085 inches in outside diameter) is pressed into the top center of the main body 37 at a cavity inlet point 103 to form an inlet passage 25.

After the main structures of the manifold 10 are assembled as just described, inserts 22 are placed into the elongated cavity 13. A sketch of an insert 22 about to be introduced into the first end 31 of the main body 37 is presented as FIG. 1. A typical insert 22 design for this first variation is presented in FIGS. 6 and 7. In this design, the overall insert length 46 is approximately 1.4 inches. The distance between the first leg 49 and second leg 52 is the leg separation distance 55, which is approximately 0.063 inches. In this first variation of a first preferred embodiment, the first leg 49 and second leg 52 are mirror images of each other. Therefore, only the details of the second leg 52 are discussed in the remaining sentences of this paragraph. The primary leg height 58 is approximately 0.125 inches, which is the perpendicular distance between the leg long side 61 and the leg short side 64. The slope angle 67 of the surface 70 passing from the leg long side 61 to the leg short side 64 is approximately 30 degrees. The distance 73 from the round end 76 to the step 79 is approximately 0.65 inches, and the distance 82 from the round end 76 to the root of the legs 85 is approximately 0.37 inches. The insert outside diameter 88 is approximately 0.182 inches, which is slightly larger than the main body inside diameter 43.

The inserts 22 are typically constructed from a plastic material. Therefore, with the insert outside diameter 88 slightly greater than the main body inside diameter 43, a fluid-tight fit is achieved when the insert 22 is forced into the elongated cavity 13 of the main body 37 (see FIG. 2). In this manner, the insert 22 provides a sealing means 106 at the ends 31, 34 of the main body 37 of the manifold 10. As an alternative to a fluid-tight fit between the inserts 22 and the main body 37, some other sealing means 106 could be placed at the first and second ends 31, 34 of the main body 37 following the placement of the inserts 22. Once the inserts 22 are in place and the ends 31, 34 of the cavity 13 are sealed, the manifold 10 is ready for use.

Referring now to FIGS. 4 and 5, a second variation of a first preferred embodiment is described. As with the first variation, this variation involves the use of an insert or inserts 22 and is primarily an alternate method of creating the main body 37 and the elongated cavity 13 therein. The main difference being that the inlet passage 25 is parallel to the longitudinal axis 28 in this variation. Construction of the manifold 10 may begin with a solid block of material, which forms the main body 37 of the manifold 10. Then, an elongated cavity 13 is made in the solid block of material by drilling or otherwise making a large diameter hole 91 therein. As an alternative to starting with a solid block, the main body 37 could be formed by casting a block with a large diameter hole 91 pre-formed therein. When a manifold 10 is produced in either of these ways, the block is directly analogous to the hollow tube used in the variation described above, and many of the dimensions provided above apply equally well here. The exterior dimensions (i.e., dimensions related to parts or surfaces that do not directly contact the fluid that is being split) may be different, but this has to do with the aesthetics of the manifold 10 and does not affect its performance. After the main body 37 and its elongated cavity 13 are formed from the block, the remaining assembly of the manifold 10 nearly duplicates the procedure described above. The main difference being where the inlet passage 25 is placed, which will be described further below.

After the main body 37 is formed, the eight smaller tubes are pressed into the bottom to intersect the elongated cavity 13 and thereby form the outlet passages 16. Although two inserts 22 could be used with this variation, as was described above with regard to the first variation, the procedure related below describes an embodiment wherein a single insert 22, running the entire length of the elongated cavity 13 from the first end 31 to the second end 34 of the main body 37, is placed in the elongated cavity 13.

A typical design for an insert 22 used in this second variation is illustrated in FIGS. 6–7. This is the same basic design used with the first variation; only the dimensions would be different. In this design, the overall insert length 46 is approximately 2.8 inches. The distance between the first leg 49 and second leg 52 is the leg separation distance 55, which is approximately 0.063 inches. In this second variation of a first preferred embodiment, the first leg 49 and second leg 52 are mirror images of each other. Therefore, only the details of the second leg 52 are discussed in the remaining sentences of this paragraph. The primary leg height 58 is approximately 0.1 inches, which is the perpendicular distance between the leg long side 61 and the leg short side 64. The slope angle 67 of the surface 70 passing from the leg long side 61 to the leg short side 64 is approximately 30 degrees. The distance 73 from the round end 76 to the step 79 is approximately 0.95 inches, and the distance 82 from the round end 76 to the root of the legs 85 is approximately 0.35 inches. The insert outside diameter 88 is approximately 0.172 inches, which is slightly larger than the main body inside diameter 43. This creates the fluid-tight fit previously described when the insert 22 is forced into the elongated cavity 13 of the main body 37. Also as discussed above, as an alternative sealing means 106 between the insert 22 and the main body 37, a separate sealing means 106 (i.e., not a physical part of the insert 22) could be placed at the ends 31, 34 of the main body 37 following the installation of the insert 22. A third alternative is to have the end cap 94 (see FIG. 4), which has the inlet passage 25 passing though it at a cavity inlet point 103 in this second variation, serve as the sealing means 106 for this end of the manifold main body 37. If a blind hole (i.e., one that does not pass clear through the material) were drilled into the block of material, it would only be necessary to seal one end of the block, since the other end would be already sealed.

Once the insert 22 is in place, and the first and second ends 31, 34 of the main body 37 are sealed using one of the sealing means 106 described above, the inlet passage 25 may be installed. In this embodiment, the inlet passage 25 is parallel to the longitudinal axis 28 and is pressed into the end cap 94 at a cavity inlet point 103 on the longitudinal axis 28. If the end cap 94 is being used to seal the elongated cavity 13, it would only be necessary to place the insert 22 into the elongated cavity 13 and mount the end cap 94 on the main body 37. Either way, the manifold 10 would then be ready for use.

Whether the elongated cavity 13 is formed from a tube (FIGS. 1–3) or a block with a hole 91 therein (FIGS. 4 and 5), it is possible to use either a single longer insert 22 or two shorter inserts 22 with either variation of the first embodiment.

FIG. 10 depicts a typical flow pattern from a first embodiment of the instant invention and demonstrates the benefit gained from this invention. This figure represents a point-by-point average of the empirical results from three tests using a manifold 10 as illustrated in FIGS. 1–3. The data were obtained using an eight-row-by-twelve-column microplate 97, part of which is illustrated in FIG. 1. Each test was conducted by dispensing 1600 $\mu$L into a manifold 10 located over the first column of eight wells 100 of a microplate 97 and then moving the manifold 10 across the columns, dispensing a total of twelve times, once per column. This process delivered approximately 200 $\mu$L into each well 100 of the microplate 97. The volume in each well 100 was measured and used to calculate the mean volume and coefficient of variation (% CV) for the entire plate 97. In addition, the mean volume from each of the eight outlet passages 16 of the manifold 10 was calculated by averaging the volume in each row of the microplate 97. Then, the percent difference between the total microplate mean and the mean volume from each outlet passage 16 was plotted as a function of the position of each outlet passage 16 along the longitudinal axis 28 of the manifold 10.

The data points of FIG. 10 enclosed in circles (these points are also connected by solid lines) are the results without the inserts 22, and the points enclosed in squares depict the more balanced flow that results when the inserts 22 depicted in FIGS. 6 and 7 are employed. As can be seen from the circled data points in FIG. 10, the flow from the two outlet passages 16 at both ends 31, 34 of the manifold 10 is above the plate mean; and the flow from the four outlet passages 16 at the center of the manifold 10 is below the plate mean. With this construction of the manifold 10, the velocity of the fluid parallel to the longitudinal axis 28 of the manifold main body 37 is greatest near the cavity inlet point 103 and almost zero at the ends 31, 34 of the manifold 10. Therefore, the flow from the outlet passages 16 near the inlet point 103 is reduced, and the flow from the outlet passages 16 generally increases as one moves in either direction away from the cavity inlet point 103. The results improved when the inserts 22 were employed, as can be seen by the data points enclosed in squares. In fact, during these tests, use of the inserts 22 reduced the total plate % CV from the 3% range to the 2% range.

Referring now to FIGS. 8–9, a second preferred embodiment of the present invention is described. In this embodiment, the manifold cavity 13 is molded with a variable cross-sectional area 19. With this method of employing the instant invention, as with the method described above, the cross-sectional area 19 of the cavity 13 is greatest where the velocity is highest in a manifold 10 that does not employ the instant invention. Similarly, the cross-sectional area 19 of the cavity 13 is the most restricted in areas where the velocity is lowest in the constant cross-sectional area design.

Referring specifically to FIG. 8, it is apparent that the exterior appearance of a manifold employing this embodiment of the instant invention resembles a manifold 10 employing the first embodiment (see, e.g., FIG. 1). The primary difference between these embodiments is only apparent from looking at the internal structure of the manifold 10, which also is revealed in FIG. 8. This embodiment has the same primary features as the first embodiment, namely, a main body 37, an inlet passage 25, a cavity inlet point 103, an elongated cavity 13, sealing means 106, first and second ends 31, 34, respectfully; and outlet passages 16. By comparing FIGS. 3 and 9, it is apparent that the elongated cavity 13 has a more complicated cross-sectional area 19 in the second embodiment (FIG. 9) than in the first embodiment (FIG. 3). The more complicated cross-sectional area stems from the fact that the shape of the inside of the main body 37 of the second embodiment serves the function of the inserts 22 used in the first embodiment and obviates the need for the inserts 22, while maintaining the advantageous results obtained from using them.

The present invention thus provides a simple, cost efficient method for splitting a quantity of fluid into substantially equal portions without dedicating costly pumps or syringes to each outlet passage 16. Whether the invention is implemented with inserts 22 (FIGS. 1-7) or by molding (FIGS. 8 and 9), it provides the additional advantage of reducing the "dead volume" of the manifold 10. Hence, by using the instant invention, the distribution problem inherent with manifolds 10 can be brought into desired tolerances, while simultaneously achieving other beneficial effects.

It is to be understood that the above-described embodiments, including the specific dimensions provided, are illustrative only and that modifications thereof may occur to those skilled in the art. Accordingly, this invention is not to be regarded as limited to the embodiments disclosed herein, but is to be limited only as defined by the appended claims.

I claim:

1. A manifold for splitting the flow of a fluid, said manifold comprising:
   a main body with an elongated cavity of constant cross-sectional area perpendicular to a longitudinal axis of said main body, said cavity being longitudinally disposed between a first end and a second end of said main body;
   an inlet passage of constant cross-sectional area communicating with an interior of said cavity at a cavity inlet point;
   a plurality of outlet passages communicating with said interior of said cavity; and
   at least two inserts, a first insert extending longitudinally into said first end of said main body and a second insert extending longitudinally into said second end of said main body, said at least two inserts comprising a first leg and second leg being separated by a constant leg separation distance before meeting at a root, the first and second legs have a sloped surface constructed so that a cross-sectional area of each of said at least two inserts perpendicular to a longitudinal axis of each of said inserts varies in a manner that balances the volume of fluid that flows from each of said outlet passages.

2. A manifold according to claim 1 which further comprises means for sealing said first end and said second end of said cavity and wherein said sealing means at said first end of said main body comprises part of said first insert and said sealing means at said second end of said main body comprises part of said second insert, said insert cross-sectional areas of said first and second inserts matching said cavity cross-sectional areas at said first end and at said second end, respectively, of said cavity of said main body.

3. A manifold according to claim 1 wherein said sloped surface connects a leg long side to a leg short side.

4. A manifold for splitting the flow of a fluid, the manifold comprising:
   a main body with an elongated cavity of constant cross-sectional area perpendicular to a longitudinal axis of said main body, said cavity being longitudinally disposed between a first end and a second end of said main body;
   an inlet passage of constant cross-sectional area communicating with an interior of said cavity at a cavity inlet point;
   a plurality of outlet passages communicating with said interior of said cavity; and
   at least one insert extending longitudinally into the cavity, the at least one insert having a cross-sectional area perpendicular to a longitudinal axis of the at least one insert that increases in a longitudinal direction from the inlet point toward either one of the ends of the main body, said at least one insert comprising a first leg and second leg being separated by a constant leg separation distance before meeting at a root, the first and second legs have a sloped surface constructed so that the cross-sectional area of the at least one insert varies, said cross-sectional area constructed in a manner that balances the volume of fluid that flows from each of said outlet passages.

5. A manifold according to claim 1 or 4 wherein said inlet passage comprises one tube.

6. A manifold according to claim 5 wherein said plurality of outlet passages comprises eight individual tubes.

* * * * *

UNITED STATES PATENT AND TRADEMARK OFFICE
CERTIFICATE OF CORRECTION

PATENT NO. : 5,334,352
DATED : August 2, 1994
INVENTOR(S) : EDGAR G. JOHNSON

It is certified that error appears in the above-indentified patent and that said Letters Patent is hereby corrected as shown below:

Claim 1, column 7, line 41, between "and" and "second" insert -- a --.

Claim 4, column 8, line 34, between "and" and "second" insert -- a --.

Signed and Sealed this

Eighteenth Day of April, 1995

Attest:

BRUCE LEHMAN

*Commissioner of Patents and Trademarks*

*Attesting Officer*